United States Patent
An et al.

(10) Patent No.: US 9,849,089 B2
(45) Date of Patent: Dec. 26, 2017

(54) HYDROGEL PARTICLE COATED WITH LIPID AND METHOD FOR MANUFACTURING SAME

(75) Inventors: Eun Jung An, Yongin-si (KR); Do Hoon Kim, Yongin-si (KR); Hyung Jun Lim, Yongin-si (KR); Jong Won Shim, Yongin-si (KR); Choon Bok Jeong, Yongin-si (KR); Lee Kyoung Kwon, Yongin-si (KR); Jun Oh Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 941 days.

(21) Appl. No.: 13/878,735

(22) PCT Filed: Oct. 12, 2011

(86) PCT No.: PCT/KR2011/007578
§ 371 (c)(1),
(2), (4) Date: Apr. 10, 2013

(87) PCT Pub. No.: WO2012/050359
PCT Pub. Date: Apr. 19, 2012

(65) Prior Publication Data
US 2013/0202667 A1 Aug. 8, 2013

(30) Foreign Application Priority Data

Oct. 14, 2010 (KR) .................. 10-2010-0100227
Jun. 21, 2011 (KR) .................. 10-2011-0060318

(51) Int. Cl.
| | | |
|---|---|---|
| *A61K 9/14* | (2006.01) | |
| *A61K 8/02* | (2006.01) | |
| *A61K 8/04* | (2006.01) | |
| *A61Q 19/00* | (2006.01) | |
| *A61K 8/55* | (2006.01) | |
| *A61K 8/73* | (2006.01) | |
| *A61K 8/14* | (2006.01) | |

(52) U.S. Cl.
CPC .............. *A61K 9/14* (2013.01); *A61K 8/0241* (2013.01); *A61K 8/042* (2013.01); *A61K 8/14* (2013.01); *A61K 8/553* (2013.01); *A61K 8/735* (2013.01); *A61Q 19/00* (2013.01); *A61K 2800/10* (2013.01); *A61K 2800/622* (2013.01); *A61K 2800/654* (2013.01)

(58) Field of Classification Search
None
See application file for complete search history.

(56) References Cited

U.S. PATENT DOCUMENTS

| | | | |
|---|---|---|---|
| 6,602,952 B1 | 8/2003 | Bentley et al. | |
| 2001/0048947 A1* | 12/2001 | Rowe | A61K 9/0019 424/486 |
| 2003/0035842 A1* | 2/2003 | Kazakov | A61K 9/127 424/497 |
| 2005/0058674 A1* | 3/2005 | Joseph | A61L 15/50 424/401 |
| 2005/0112151 A1* | 5/2005 | Horng | A61K 8/0212 424/401 |
| 2006/0061336 A1 | 3/2006 | Anghel et al. | |
| 2009/0098207 A1* | 4/2009 | Malakhov | A61K 9/5089 424/489 |
| 2011/0020428 A1* | 1/2011 | Zeng | A61K 9/06 424/450 |

FOREIGN PATENT DOCUMENTS

| | | |
|---|---|---|
| JP | 200553866 A | 3/2005 |
| KR | 100186908 | 12/1998 |
| KR | 10-2006-0028604 | 3/2006 |
| KR | 100852944 | 8/2008 |
| WO | 9704747 | 2/1997 |
| WO | 2009020067 A1 | 2/2009 |

OTHER PUBLICATIONS

International Search Report—PCT/KR2011/007578 dated May 16, 2012.
Written Opinion—PCT/KR2011/007578 dated May 16, 2012.
Korean Office Action dated Aug. 25, 2017, in corresponding patent application No. 1020110060318 (W/English Translation).

* cited by examiner

*Primary Examiner* — Robert A Wax
*Assistant Examiner* — Randeep Singh
(74) *Attorney, Agent, or Firm* — Cantor Colburn LLP

(57) ABSTRACT

The present invention relates to hydrogel particles coated with lipid, which are made from dispersing hydrogel particles in an organic solvent in which lipids are dissolved, and to a method for manufacturing same. Unlike the existing method for manufacturing hydrogel core vesicles, the present invention can effectively manufacture same by using an emulsification method, without involving the steps of chemical treatment of the surface of hydrogels or dilution, thereby facilitating mass production and preventing the decrease of drug encapsulation efficiency. The present method could be widely used for research on delivery carriers of oil/water-soluble active material or cell structure reproduction and more particularly, a keratinocyte mimetic of the present invention containing natural moisturizing factors can contain a large quantity of bound water for a long time, thereby exhibiting superior capability to retain moisture and moisturize, and providing a composition for an ingredient in cosmetics for moisturizing.

13 Claims, 4 Drawing Sheets

[Fig. 1]
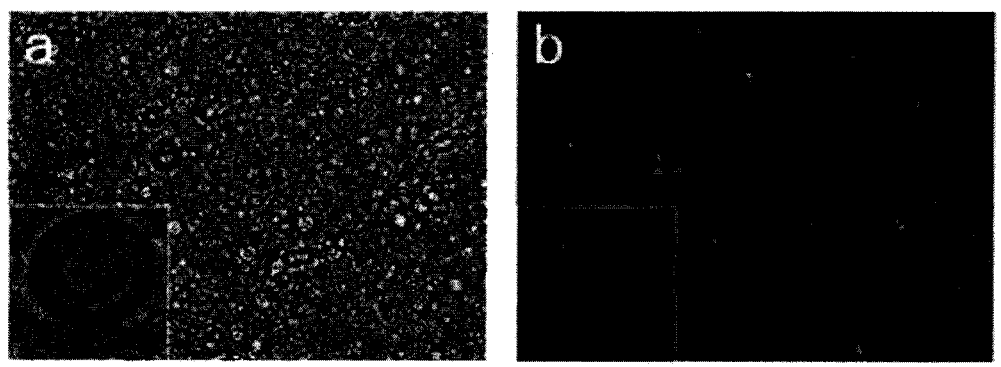
[Fig. 2]
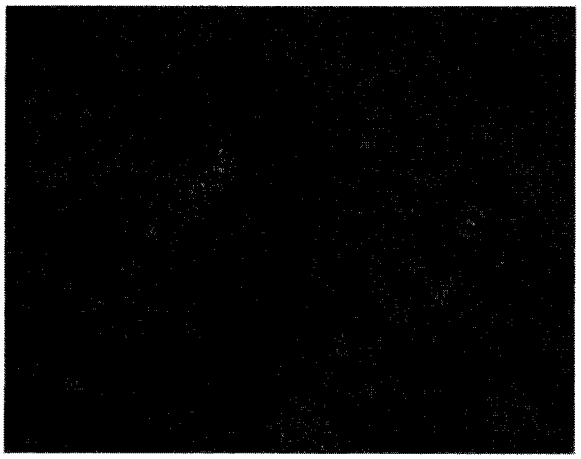

[Fig. 3]
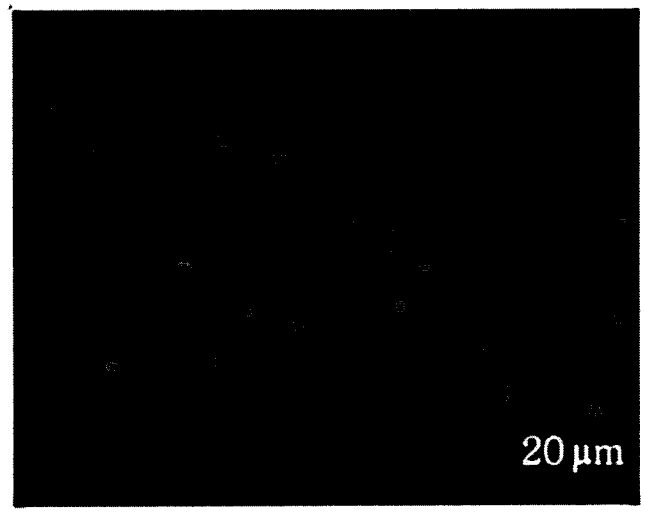
[Fig. 4]
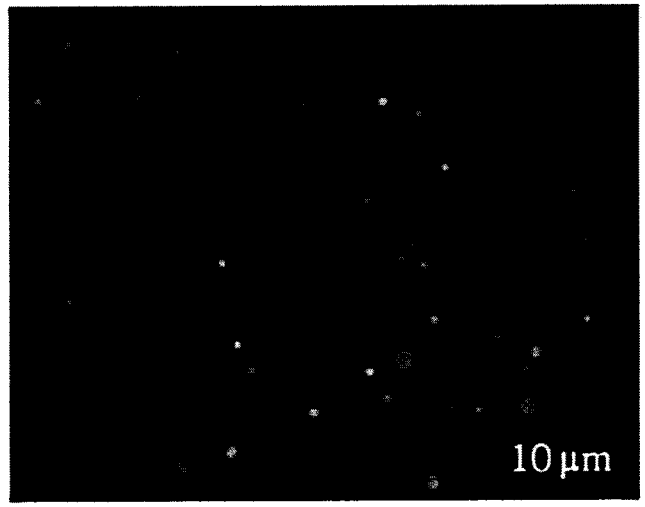

[Fig. 5]
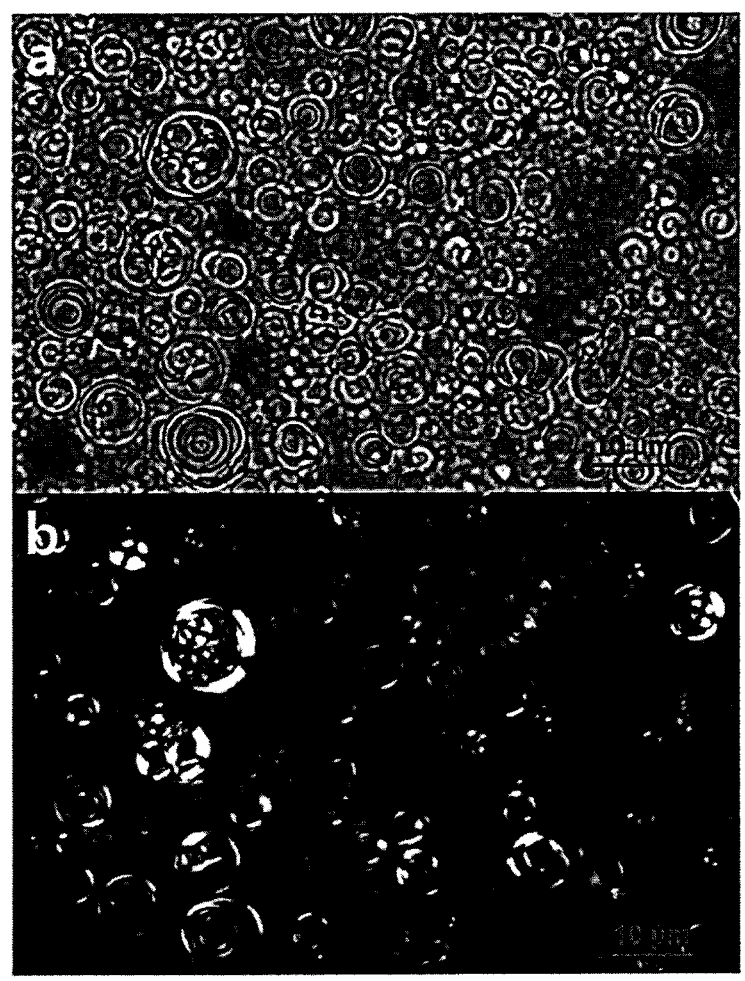

[Fig. 6]
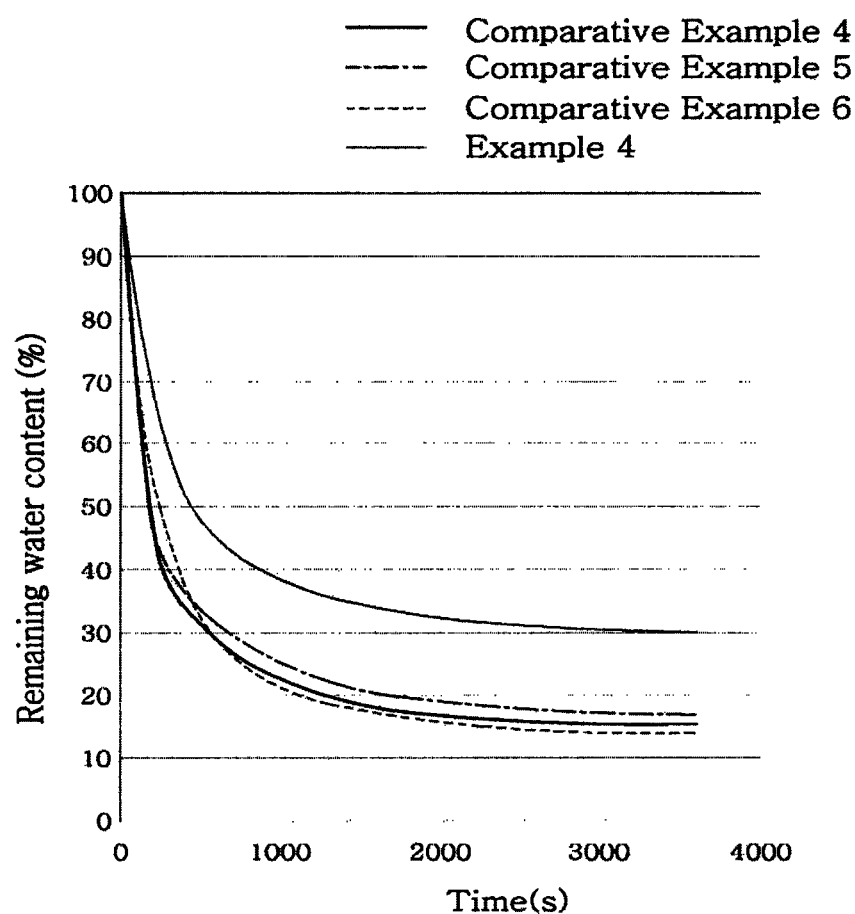

HYDROGEL PARTICLE COATED WITH LIPID AND METHOD FOR MANUFACTURING SAME

TECHNICAL FIELD

The present disclosure relates to a method for coating the surface of a hydrogel particle with lipid.

BACKGROUND ART

Hydrogel core vesicles, also known as lipobeads, in which the surface of crosslinked hydrogel particles is surrounded by a lipid bilayer, are a new type of vesicles exhibiting the characteristics of both liposomes and hydrogel particles and are similar to the cytoskeleton in structure or shape. Owing to such structural characteristics, the hydrogel core vesicles are used for analysis of lipid bilayer characteristics and study of cellular models, e.g. biosensors. It can carry hydrophilic/hydrophobic materials inside/outside thereof and, when stimulation-sensitive hydrogels are used as the core, it can serve as stimulation-sensitive drug carriers capable of adjusting the release of materials included in response to an external stimulus.

Until now, two methods are known for the preparation of the hydrogel core vesicle. They are: mixing hydrogel particles with a liposome solution to induce adsorption of the liposome on the surface of the hydrogel particles; and preparing a liposome containing hydrogel-forming materials, i.e. monomer, initiator and crosslinking agent, in the inner aqueous phase and performing polymerization inside the liposome. The first method requires pretreatment of covalently bonding a fatty acid, lecithin, etc. on the hydrogel surface for effective adsorption of the lipid bilayer. In addition, the second method requires dilution with excess water to prevent polymerization of the monomers not included inside the liposome. As such, both methods involve complicated processes and are inapplicable to mass production.

Nowadays, due to artificial temperature control through air conditioning owing to change in environments or lifestyles, stresses resulting from everyday lives and skin stresses resulting from environmental pollution, frequent makeup and face washing, and natural skin aging, or the like, many people suffer dry, rough, crumbly and dark skin, etc because of loss of moisture from the stratum corneum and need skin moisturizers increasingly.

The skin is composed of largely three layers of the epidermis, the dermis and the subcutaneous tissue in order from outside. It protects internal organs of the body from change in temperature and humidity, UV light and other physical and chemical stimuli from the external environment. Especially, the epidermis plays an important role of preventing loss of water from the body. The epidermis consists of, in order from outside, the stratum corneum, the stratum granulosum, the stratum spinosum and the stratum basale. The cells of the stratum corneum function like bricks and lipid between the keratinocytes function like mortar, thus forming the skin barrier. In the keratinocytes of a healthy person, natural moisturizing factors (NMFs) which help to retain water are present at high concentrations. For example, since amino acids are water-soluble, they effectively bind to water and prevent the loss of water from the skin.

Recently, it was found out that the water holding capacity of preventing the skin from drying can be retained when the keratinocytes in the stratum basale are normally differentiated into the keratinocytes of the outermost stratum corneum. That is to say, during keratinization, the cells produce a natural moisturizing factor and intercellular lipid and, as a result thereof, the stratum corneum becomes rigid and flexible and can function as a barrier. As a person becomes older, the skin becomes drier. Physiologically, it means increased turnover time of the stratum corneum, decreased lipid synthesis ability of epidermal cells and decreased level of a moisturizing factor and lipid in the stratum corneum. Therefore, by facilitating the differentiation of keratinocytes and thereby inducing enhancement of the skin barrier, it will be possible to enhance water holding capacity of the skin and provide protection from external environment.

Until recently, humectants that absorb water or occlusive moisturizers that prevent loss of water have been used to retain water in the stratum corneum. As for the humectant, glycerin, propylene glycol, 1,3-butylene glycol, polyethylene glycol, sorbitol, and sodium 2-pyrrolidone-5-carboxylate, etc. are available, but they feel quite sticky when applied on the skin. As for the occlusive moisturizer, lipid such as ceramide, essential fatty acids, and lipid complexes, or the like have been used. But, it is difficult to keep the stability of emulsions formulation or prepare transparent gel products. Few studies have been reported on effective moisturizers featuring the functions of both the humectants and the occlusive moisturizers.

DISCLOSURE

Technical Problem

The present disclosure is directed to providing hydrogel particles coated with lipid capable of containing an active material with high efficiency, which can be prepared effectively without involving a complicated process, and a method for preparing same. The present disclosure is also directed to providing a keratinocyte mimetic containing a natural moisturizing factor exhibiting superior moisturizing effect, which contains the natural moisturizing factor at high concentrations similarly to skin keratinocytes and thus has improved water holding capacity and is surrounded by lipid lamellar structure to prevent loss of water, a method for preparing same and a cosmetic composition for moisturization containing same.

Technical Solution

In a general aspect, the present disclosure provides hydrogel particles coated with lipid, which are prepared by dispersing hydrogel particles in an organic solvent in which lipid is dissolved, and a method for preparing same.

In an exemplary embodiment of the present disclosure, the preparation method may include:
(a) dissolving lipid in an organic solvent;
(b) dispersing hydrogel particles prepared from a water-soluble polymer and a water-soluble crosslinking agent in the organic solvent in which the lipid is dissolved; and
(c) adding water to the resulting dispersion of the above (b) and distilling under a reduced pressure.

In another general aspect, the present disclosure provides hydrogel particles coated with lipid, comprising: hydrogel particles; and a lipid coating layer surrounding the hydrogel particles, which are prepared by dispersing the hydrogel particles in an organic solvent in which the lipid is dissolved.

In an exemplary embodiment of the present disclosure, the hydrogel particles coated with lipid may be a keratinocyte mimetic and the keratinocyte mimetic may include:

hydrogel particles containing a natural moisturizing factor; and a lipid coating layer surrounding the hydrogel particles.

In another general aspect, the present disclosure provides a cosmetic composition containing the hydrogel particles coated with lipid as an active ingredient, wherein the hydrogel particles contain an active material.

Advantageous Effects

Unlike the existing method for preparing a hydrogel core vesicle, the present disclosure allows effective preparation in a single batch via a simple process without involving chemical treatment of the hydrogel surface or dilution. Accordingly, production cost is low and mass production is possible. Further, the present disclosure can prevent decrease of drug encapsulation efficiency and have good loading efficiency. The method of the present disclosure can be widely used for research on carriers of various oil/water-soluble active materials or drugs, or cell structure reproduction. In particular, a keratinocyte mimetic of the present disclosure containing a natural moisturizing factor can contain a large quantity of bound water for a long time and thus exhibits superior water holding capacity and moisturizing effect. The present disclosure also provides a cosmetic composition for moisturization containing same as a moisturizing ingredient.

DESCRIPTION OF DRAWINGS

FIG. 1 shows an optical microscopic image (a) and a polarization microscopic image (b) of hydrogel particles coated with lipid according to an exemplary embodiment of the present disclosure.

FIG. 2 shows an optical microscopic image of particles according to a comparative example.

FIG. 3 shows a fluorescence microscopic image of hydrogel particles coated with lipid containing Nile red according to an exemplary embodiment of the present disclosure.

FIG. 4 shows a fluorescence microscopic image of hydrogel particles coated with lipid containing FITC-dextran according to an exemplary embodiment of the present disclosure.

FIG. 5 shows an optical microscopic image (a) and a polarization microscopic image (b) of a keratinocyte mimetic containing a natural moisturizing factor according to an exemplary embodiment of the present disclosure.

FIG. 6 shows water content of a keratinocyte mimetic containing a natural moisturizing factor according to an exemplary embodiment of the present disclosure.

BEST MODE

Exemplary embodiments of the present disclosure are now described in detail to fully convey the scope of the present disclosure to those of ordinary skill in the art.

A method for preparing hydrogel particles coated with lipid according to the present disclosure includes:
(a) dissolving lipid in an organic solvent;
(b) dispersing hydrogel particles prepared from a water-soluble polymer and a water-soluble crosslinking agent in the organic solvent in which the lipid is dissolved; and
(c) adding water to the resulting dispersion of the above (b) and distilling under a reduced pressure.

In the process of (a), the lipid may be one or more selected from a group consisting of soybean lecithin, phosphatidylcholine, phosphatidylserine, phosphatidylethanolamine, phosphatidylglycol and hydrogenated phosphatidylcholine. Specifically, it may be soybean lecithin.

A content of the lipid may be 2-10 times a dry weight of the hydrogel. If the content of the lipid is equal to or less than 2 times of the dry weight of the hydrogel, a large amount of the hydrogel may remain uncoated. And, if the content is equal to or more than 10 times the dry weight of the hydrogel, most of the hydrogel forms a liposome.

The organic solvent may include: a main organic solvent; and a $C_1$-$C_6$ alcohol, wherein the main organic solvent is a nonpolar solvent having a boiling point of 40-110° C. and is selected from a group consisting of a hydrocarbon, a halogenated hydrocarbon and an aromatic hydrocarbon. As non-limiting examples, the main organic solvent may be one or more selected from a group consisting of methylene chloride, chloroform, hexane, heptane, isooctane, cyclohexane, benzene, toluene, xylene and dimethyl ether. The alcohol serves as an auxiliary surfactant that helps the dissolution of the lipid and stably disperses the hydrated hydrogel in the main organic solvent. The alcohol may be a $C_1$-$C_6$ alcohol. As non-limiting examples, it may be methanol, ethanol or propanol.

A content of the alcohol may be 20-70% of a content of the main organic solvent. If the content of the alcohol is equal to or less than 20% of the content of the main organic solvent, the lipid may not dissolve or phase separation may occur between the hydrated hydrogel and the organic solvent. And, if the content of the alcohol is equal to or more than 70% of the content of the main organic solvent, the lipid may aggregate without forming particles.

In the process of (b), the hydrogel particles are prepared by crosslinking a water-soluble polymer microparticle or nanoparticle with a crosslinking agent. The crosslinking is performed by mixing an oil phase in which a surfactant is dissolved with an aqueous phase in which the water-soluble polymer and the water-soluble crosslinking agent are dissolved and thus forming a W/O emulsion. The final product is washed several times with water to remove the surfactant.

The water-soluble polymer may be one or more selected from a group consisting of hyaluronic acid and a salt thereof, polyvinyl alcohol, polyvinylpyrrolidone, maleic anhydride/vinyl ether copolymer, gelatin, alginate, hydroxyethyl methacrylate, carrageenan, hydroxyethyl cellulose, silicone rubber, agar, hydroxypropyl cellulose, hydroxypropyl methylcellulose, methyl cellulose, carboxyvinyl copolymer, polyethylene oxide, polyethylene glycol, polyacrylamide, poly(hydroxyethyl methacrylate), polydioxolane, polyacrylic acid, polyacryl acetate, polyacrylamide and polyvinyl chloride.

The crosslinking agent may be one or more selected from a group consisting of ethylene glycol, glycerin, polyoxyethylene glycol, calcium chloride, bisacrylamide, diaryl phthalate, diaryl adipate, 1,4-butanediol diglycidyl ether, polyethylene glycol diglycidyl ether, polypropylene glycol diglycidyl ether, triglycerin diglycidyl ether, triarylamine and glyoxal.

Specifically, in the process of (c), water may be added slowly. The hydrogel swells as water is added. After the organic solvent is removed by distillation under a reduced pressure, the lipid is spontaneously oriented and coated on the surface of the hydrogel particles.

In an exemplary embodiment of the present disclosure, an active material may be contained in the hydrogel particles coated with lipid.

An oil-soluble active material may be contained in the hydrogel particles coated with lipid by further dissolving oil-soluble active materials or drug in the organic solvent in the process of (a).

A water-soluble active material may be contained in the hydrogel particles coated with lipid by, simultaneously with the process of (b) or before or after the process of (b), further adding water-soluble active materials or drug. That is to say, the water-soluble active material may be added to the organic solvent in which the lipid is dissolved and then the hydrogel particle may be dispersed therein. Alternatively, the hydrogel particle and the water-soluble active material may be dispersed simultaneously or the water-soluble active material may be added to the dispersion of the hydrogel particles.

As non-limiting examples, the active material may be selected from a group consisting of L-ascorbic acid and a derivative thereof, epigallocatechin-3-gallate and a derivative thereof, retinol, retinyl acetate, retinyl palmitate, tocopherol, tocopheryl acetate, tocopheryl linoleate, tocopheryl nicotinate, linoleic acid, coenzyme $Q_{10}$, resveratrol, lipoic acid, thymol trimethoxycinnamate, curcumin, tetrahydrocurcumin, oleanolic acid, ursolic acid, betulin, betulinic acid, diosmetin, quercetin, lycopene, kaempferol, luteolin, animal/plant extract, kojic acid and a derivative thereof, ceramide, peptide compound, amino acid, caffeine, water-soluble functional extract and oil-soluble functional extract.

In an exemplary embodiment of the present disclosure, a natural moisturizing factor may be contained in the hydrogel particles coated with lipid as the water-soluble active material. In this case, a keratinocyte mimetic is obtained. Specifically, a method for preparing the keratinocyte mimetic includes: (a) dissolving lipid in an organic solvent; (b) dispersing hydrogel particles prepared from a natural moisturizing factor, a water-soluble polymer and a water-soluble crosslinking agent in the organic solvent in which the lipid is dissolved; and (c) adding water to the resulting dispersion and distilling under a reduced pressure.

A mixture of the natural moisturizing factor (NMF) may be any mixture prepared with a similar composition ratio to a natural moisturizing factor existing in the stratum corneum of human skin. Specifically, the natural moisturizing factor may include one or more selected from a group consisting of amino acid, sodium pyrrolidone carboxylate, sodium lactate and urea. More specifically, the natural moisturizing factor may be amino acid. An exemplary composition ratio of the moisturizing factor is described in Table 1.

TABLE 1

Composition ratio of a natural moisturizing factor

| Ingredients | Contents (%) |
|---|---|
| Sodium pyrrolidone carboxylate | 12 |
| Sodium lactate | 5 |
| Urea | 7 |
| Serine | 18.2 |
| Glycine | 9.1 |
| Arginine | 3.2 |
| Glutamic acid | 2.3 |
| Tyrosine | 0.5 |
| Alanine | 6.6 |
| Purified water | To 100 |

The amino acid may include one or more selected from a group consisting of serine, glycine, arginine, glutamic acid, tyrosine and alanine, but is not necessarily limited thereto.

Specifically, a content of the natural moisturizing factor may be 5-30 wt % of a content of the hydrogel particles coated with lipid, i.e. the keratinocyte mimetic. If the content of the natural moisturizing factor is equal to or less than 5 wt % of the content of the hydrogel particles coated with lipid, moisturizing effect may be insufficient. And, if the content of the natural moisturizing factor is equal to or more than 30 wt % of the content of the hydrogel particles coated with lipid, it may give off unpleasant odor characteristic of the natural moisturizing factor and may negatively affect the stability of a cosmetic product by interfering with the formation of a structure.

The present disclosure further provides hydrogel particles coated with lipid, including: hydrogel particles; and a lipid coating layer surrounding the hydrogel particles, which are prepared by dispersing the hydrogel particles in an organic solvent in which lipid is dissolved.

The present disclosure further provides hydrogel particles coated with lipid containing a water/oil-soluble active material or a water/oil-soluble drug inside the hydrogel particles. The hydrogel particles coated with lipid may be used as an active material carrier or a drug carrier.

In an exemplary embodiment of the present disclosure, the hydrogel particles coated with lipid may be a keratinocyte mimetic and the keratinocyte mimetic may include: hydrogel particles containing a natural moisturizing factor; and a lipid coating layer surrounding the hydrogel particles.

The keratinocyte mimetic of the present disclosure mimics the structural characteristics of the keratinocyte which contains a large quantity of bound water owing to a natural moisturizing factor and reduces loss of water being surrounded by the cornified envelope and intercellular lipid. For this, the lipid vesicle having a hydrogel core is prepared and the natural moisturizing factor is contained therein. The hydrogel and the natural moisturizing factor allow capturing of a large quantity of bound water and the lipid bilayer assembled with a lamellar structure prevents loss of the bound water, thus providing excellent moisturizing effect.

The present disclosure further provides a cosmetic composition containing hydrogel particles coated with lipid as an active ingredient, wherein the hydrogel particles contain an active material. In particular, the present disclosure provides a cosmetic composition containing a keratinocyte mimetic, which is hydrogel particles coated with lipid containing a natural moisturizing factor, as an active ingredient.

A content of the active ingredient may be 0.1-20 wt % of based on the total weight of the composition, although not being specially limited thereto. When the content of the active ingredient is in the above range, superior effect may be achieved without a side effect.

The formulation of the cosmetic composition is not specially limited and may be determined appropriately depending on purposes. For example, the cosmetic composition may be prepared into one or more formulation selected from a group consisting of skin lotion, skin softener, skin toner, astringent, lotion, milk lotion, moisturizing lotion, nourishing lotion, massage cream, nourishing cream, moisturizing cream, hand cream, foundation, essence, nourishing essence, pack, soap, cleansing foam, cleansing lotion, cleansing cream, body lotion and body cleanser, without being limited thereto.

When the formulation of the present disclosure is paste, cream or gel, animal fiber, plant fiber, wax, paraffin, starch, tragacanth, cellulose derivatives, polyethylene glycol, silicone, bentonite, silica, talc, or zinc oxide, etc. may be used as a carrier ingredient.

When the formulation of the present disclosure is powder or spray, lactose, talc, silica, aluminum hydroxide, calcium silicate or polyamide powder may be used as a carrier ingredient. Especially, when the formulation is spray, it may further contain a propellant such as chlorofluorohydrocarbon, propane/butane or dimethyl ether.

When the formulation of the present disclosure is solution or emulsion, a solvent, a solubilizer or an emulsifier may be used as a carrier ingredient. For example, water, ethanol, isopropanol, ethyl carbonate, ethyl acetate, benzyl alcohol, benzyl benzoate, propylene glycol, 1,3-butyl glycol oil, glycerol aliphatic ester, polyethylene glycol or fatty acid ester of sorbitan may be used.

When the formulation of the present disclosure is suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier ingredient.

When the formulation of the present disclosure is surfactant-containing cleanser, aliphatic alcohol sulfate, aliphatic alcohol ether sulfate, sulfosuccinic monoester, isethionate, imidazolinium derivatives, methyl taurate, sarcosinate, fatty acid amide ether sulfate, alkyl amidobetaine, aliphatic alcohol, fatty acid glyceride, fatty acid diethanolamide, vegetable oil, lanolin derivatives, ethoxylated glycerol fatty acid ester, etc. may be used as a carrier ingredient.

The cosmetic composition may further contain, in addition to the keratinocyte mimetic, a functional additive and other ingredients commonly included in a cosmetic composition. The functional additive may be selected from a group consisting of water-soluble vitamin, oil-soluble vitamin, polypeptide, polysaccharide, sphingolipid and seaweed extract.

The cosmetic composition of the present disclosure may further mix, in addition to the functional additive, the ingredients commonly included in a cosmetic composition, as necessary. For example, the additionally included ingredients may be ingredient of fat and oil, moisturizer, emollient, surfactant, organic or inorganic pigment, organic powder, UV absorber, antiseptic, sterilizer, antioxidant, plant extract, pH adjuster, alcohol, colorant, fragrance, blood circulation stimulant, skin cooler, deodorant, purified water, etc.

The present disclosure further provides a pharmaceutical composition containing hydrogel particles coated with lipid as an active ingredient, wherein the hydrogel particles contain drugs.

The pharmaceutical composition may further contains a pharmaceutical adjuvant such as antiseptic, stabilizer, hydrant, emulsification promoter, salt for control of osmotic pressure, and/or buffer, etc. and other therapeutically useful materials and may be prepared into various formulations for oral or parenteral administration according to commonly employed methods. A formulation for parenteral administration may be one for transdermal administration and may be, for example, lotion, ointment, gel, cream, patch or spray, but is not limited thereto.

Determination of a dosage of the active ingredient is within the level of those skilled in the art. A daily dosage of the drug varies depending on various factors such as progress and duration of a condition to be treated, age and health condition of a subject, presence of complication, or the like. A dosage of the composition for an adult is generally 1 µg/kg to 200 mg/kg, specifically 50 µg/kg to 50 mg/kg. The administration can be made 1-3 times a day. However, the administration dosage does not limit the scope of the present disclosure by any means.

Hereinafter, the present disclosure will be described in detail through examples and comparative examples. However, the following examples and comparative examples are for illustrative purposes only and it will be apparent to those of ordinary skill in the art that the scope of the present disclosure is not limited by the examples.

Example 1

Preparation of Hyaluronic Acid Hydrogel Coated with Lipid

Hyaluronic acid hydrogels coated with lipid of Example 1 and Comparative Examples 1-2 were prepared with compositions described in Table 2. Soybean lecithin was completely dissolved in an organic solvent and hyaluronic acid hydrogel particles in powder form were dispersed therein. Then, distilled water was slowly added while agitating with a mixer. Finally, hyaluronic acid hydrogels coated with lipid were obtained by completely removing the remaining organic solvent using a rotary evaporator. The method used to prepare the hyaluronic acid hydrogel particles in these examples is disclosed in Korean Patent Application No. 10-2007-0015864 which was filed by the applicants of the present disclosure.

TABLE 2

| Ingredients (wt %) | Example 1 | Comparative Example 1 | Comparative Example 2 |
|---|---|---|---|
| Soybean lecithin | 5 | 5 | 5 |
| Ethanol | 7 | — | 7 |
| Methylene chloride | 15 | 15 | — |
| Hyaluronic acid hydrogel particles | 1 | 1 | 1 |
| Purified water | to 100 | to 100 | to 100 |

Test Example 1

Observation of Prepared Particles

The particles prepared in the Example 1 and Comparative Examples 1-2 were observed using an optical microscope. As seen from FIG. 1, the surface of the hydrogel particles prepared in Example 1 was surrounded by lecithin. The polarization microscopic image revealed that lecithin is directionally oriented and has vesicles form oriented around the particles since polarization was observed on the particle surface. In contrast, the particles prepared in Comparative Example 1 were not coated with lecithin since swollen hyaluronic acid particles and small lecithin aggregates were observed as shown in FIG. 2. It is because phase separation occurred between the hydrogel particles and the organic solvent phase during the preparation process since ethanol was not included unlike Example 1. In case of Comparative Example 2, hydrogel core vesicles were not formed and particle aggregation was observed with the naked eyes immediately after ethanol was removed.

Examples 2-3

Introduction of Active Material Into Hydrogel Coated with Lipid

Hydrogels coated with lipid in which Nile red, an oil-soluble active material, and a water-soluble active material- FITC-dextran (Mw 10,000), are contained of Examples 2-3 were prepared according to the same procedure as Example 1, with compositions described in Table 3. Nile red was dissolved in an organic solvent together with lipid and dextran was dissolved in 5 g of distilled water and then slowly added to the organic solvent before pure distilled water was added thereto. Observation of the prepared hydrogels coated with lipid under a fluorescence microscope revealed that Nile red and FITC-dextran are contained in the lipid shell and in the hydrogel core, respectively (FIGS. 3 and 4).

In Comparative Example 3, a method for preparing hydrogel core vesicles disclosed in literature was modified. Soybean lecithin was dissolved inside a round-bottom flask by adding chloroform. Then, a lipid bilayer was formed on the bottom of the flask through distillation under a reduced pressure using a rotary evaporator. After sufficiently swelling hyaluronic acid hydrogel particles by dispersing in distilled water in which a water-soluble material was dissolved, the dispersion was added to the flask containing the lipid bilayer and mixed while warming to 50° C. or higher.

TABLE 3

| Ingredients (wt %) | Example 2 | Example 3 | Comparative Example 3 |
|---|---|---|---|
| Soybean lecithin | 5 | 5 | 5 |
| Ethanol | 7 | 7 | — |
| Methylene chloride | 15 | 15 | — |
| Chloroform | — | — | 15 |
| Hyaluronic acid hydrogel particles | 1 | 1 | 1 |
| FITC-dextran | — | 0.05 | 0.05 |
| Nile red | 0.01 | — | — |
| Purified water | to 100 | to 100 | to 100 |

Test Example 2

Comparison of Encapsulation Efficiency of Water-Soluble Material in Particles 50 mL of the dispersion of the hydrogel particles prepared in Example 3 or Comparative Example 3 was centrifuged at 5000 rpm for 10 minutes. After removing the supernatant, the remainder was dispersed again in distilled water. This procedure was repeated at least 3 times to completely remove the water-soluble material remaining not encapsulated in the particles. 50 mL of the washed hydrogel coated with lipid was added to 1 mL of dimethyl sulfoxide and incubated for 1 hour. After adding 2 mL of a 0.5% sodium dodecyl sulfate/0.01 N sodium hydroxide solution and allowing to stand at room temperature for 1 hour, the FITC-dextran contained inside the particle was dissolved out and quantitated using a fluorospectrometer. As seen from Table 4, the hydrogel coated with lipid prepared according to the present disclosure showed higher encapsulation efficiency of the water-soluble material as compared to the existing method based on liposome adsorption.

TABLE 4

| | Encapsulation efficiency |
|---|---|
| Example 2 | 11.4 ± 2.6% |
| Comparative Example 3 | 3.2 ± 0.8% |

Example 4

Preparation of Keratinocyte Mimetic Containing a Natural Moisturizing Factor

A keratinocyte mimetic containing a natural moisturizing factor of Example 4 was prepared with the composition described in Table 5.

First, soybean lecithin was completely dissolved in an organic solvent and then dispersed into a w/o emulsion by adding a natural moisturizing factor. In order to adjust solid content to 16% such that a content of the natural moisturizing factor excluding purified water was 63.9 wt %, 25% of the natural moisturizing factor was mixed with purified water.

Then, hyaluronic acid hydrogel particles were prepared. 4.5 g of A-P135, a surfactant, was dissolved in 105 g of dodecane using an agitator. At the same time, 1.35 g of hyaluronic acid (Mn=1,500,000) and 1.3 g of butylene glycol diglycidyl ether, a water-soluble crosslinking agent, were dissolved in in 45 g of a 0.1 N sodium hydroxide aqueous solution using an agitator. The 0.1 N sodium hydroxide aqueous solution in which the hyaluronic acid and the water-soluble crosslinking agent were dissolved was slowly added to the dodecane in which the surfactant was dissolved and mixed for 10 minutes while agitating at a speed of 7000 rpm. Thus prepared w/o emulsion was transferred to a reactor and subjected to crosslinking by heating to 60° C. while agitating such that the w/o emulsion was maintained. While continuously agitating, the temperature of the reactor was lowered to room temperature and acetic acid was added to neutralize the aqueous phase of the w/o emulsion. Crosslinking carried out for 2 days while agitating the w/o emulsion at room temperature. After the crosslinking was completed, hyaluronic acid hydrogel nanoparticles were collected from the aqueous phase of the w/o emulsion, washed and then dried in vacuum at 90° C. for 24 hours.

Thus obtained hyaluronic acid hydrogel particles in powder form were dispersed in the w/o emulsion in which the natural moisturizing factor was dispersed and distilled water was added while agitating using a mixer. Subsequently, the remaining organic solvent was completely removed using a rotary evaporator and a keratinocyte mimetic was obtained.

Comparative Example 4

A keratinocyte mimetic of Comparative Example 4 was prepared in the same manner as in Example 4, but a glycerin aqueous solution was contained instead of a natural moisturizing factor, as described in Table 5.

Comparative Example 5

Hydrogel core vesicles of Comparative Example 5 was prepared according to the previously known film hydration method. First, 5 g of soybean lecithin was added to a round-bottom flask and dissolved by adding 15 g of chloroform. Then, a lipid bilayer was formed on the bottom of the flask through distillation under a reduced pressure using a rotary evaporator. After sufficiently swelling hyaluronic acid hydrogel particles by dispersing in distilled water in which a natural moisturizing factor was dissolved, the dispersion was added to the flask containing the lipid bilayer and mixed while warming to 50° C. or higher.

Comparative Example 6

In Comparative Example 6, a natural moisturizing factor was simply mixed with purified water to observe the evaporation behavior of the natural moisturizing factor. A content of the natural moisturizing factor was set to 19% for easy comparison with the water evaporation behavior depending on solid content (lipid, hydrogel, natural moisturizing factor) of Example 4.

TABLE 5

| Ingredients (wt %) | Example 4 | Comparative Example 4 | Comparative Example 5 | Comparative Example 6 |
|---|---|---|---|---|
| Soybean lecithin | 5 | 5 | 5 | — |
| Hyaluronic acid hydrogel particles | 1 | 1 | 1 | — |
| Natural moisturizing factor (63.9%) | 10 | — | 10 | 19 |
| Glycerin aqueous solution (63.9%) | — | 10 | — | — |
| Ethanol | 7 | 7 | — | — |
| Methylene chloride | 15 | 15 | — | — |
| Chloroform | — | — | 15 | — |
| Purified water | to 100 | to 100 | to 100 | to 100 |

Preparation Example 1

Preparation of Cosmetic Compositions Containing Keratinocyte Mimetic

O/W and gel forms were prepared as described in Tables 6 and 7 (unit: wt %).

TABLE 6

| | Ingredients (wt %) | Example 5 | Comparative Example 7 |
|---|---|---|---|
| Oily ingredient | Stearic acid | 2.5 | 2.5 |
| | Cetearyl alcohol | 0.5 | 0.5 |
| | Glyceryl stearate/PEG 100 stearate | 1.5 | 1.5 |
| | Cetyl octanoate | 4.0 | 4.0 |
| | Isopropyl palmitate | 4.0 | 4.0 |
| | 2-Octyldodecanol | 4.0 | 4.0 |
| | Dimethicone | 1.0 | 1.0 |
| | Cyclomethicone | 3.0 | 3.0 |
| | p-Oxybenzoic acid ester | Adequate | Adequate |
| | Purified water | To 100 | To 100 |
| Aqueous ingredient 1 | Butylene glycol | 5.0 | 5.0 |
| | Disodium EDTA | Adequate | Adequate |
| | TEA | Adequate | Adequate |
| | Imidazolidinyl urea | Adequate | Adequate |
| | Carbomer 1% aqueous solution | 12 | 12 |
| Aqueous ingredient 2 | Keratinocyte mimetic prepared in Example 4 | 5 | — |

TABLE 7

| | Ingredients (wt %) | Example 6 | Comparative Example 8 |
|---|---|---|---|
| Aqueous ingredient 1 | Purified water | To 100 | To 100 |
| | Butylene glycol | 5.0 | 5.0 |
| | Disodium EDTA | Adequate | Adequate |
| | Trehalose | 1 | 1 |
| | PEG 75 | 1 | 1 |
| | Potassium hydroxide | Adequate | Adequate |
| Aqueous ingredient 2 | Carbomer 1% aqueous solution | 20 | 20 |
| | Xanthan gum | 0.1 | 0.1 |
| Aqueous ingredient 3 | Keratinocyte mimetic prepared in Example 4 | 5.0 | — |
| Alcohol ingredient | Ethanol 95% | 3.0 | 3.0 |
| | Polyoxyethylene hydrogenated castor oil | 0.3 | 0.3 |
| | p-Oxybenzoic acid ester | Adequate | Adequate |

Example 5 and Comparative Example 7

(1) The oily ingredient was uniformly mixed while heating at 70-75° C.
(2) The aqueous ingredient 1 was uniformly dissolved and mixed while heating at 70-75° C.
(3) The mixture of (1) was added to the mixture of (2) while agitating with temperature maintained at 70-75° C. Thus prepared emulsion was cooled to 50° C. or lower. Then, the aqueous ingredient 2 was added and dispersed uniformly through agitation.

Example 6 and Comparative Example 8

(1) The aqueous ingredient 1 was uniformly mixed.
(2) The alcohol ingredient was uniformly mixed.
(3) The aqueous ingredient 2 was slowly added to the mixture of (1) while agitating. Subsequently, the alcohol ingredient was added to obtain a gel form. Then, the aqueous ingredient 3 was added and dispersed uniformly through agitation.

Test Example 3

Comparison of Encapsulation Efficiency of a Natural Moisturizing Factor in Particles 50 mL of the keratinocyte mimetic prepared in Example 4 or Comparative Example 5 was centrifuged at 5000 rpm for 10 minutes. The encapsulation efficiency of the natural moisturizing factor was evaluated by analyzing the amount of serine remaining not contained in the particles in the supernatant by HPLC. As seen from Table 8, the keratinocyte mimetic prepared according to the preparation method of the present disclosure exhibited at least 3 times higher encapsulation efficiency of the natural moisturizing factor than that prepared by the existing method based on liposome adsorption.

TABLE 8

| | Encapsulation efficiency |
|---|---|
| Example 4 | 12.6 ± 2.8% |
| Comparative Example 5 | 2.8 ± 0.9% |

Test Example 4

Measurement of Water Evaporation Behavior

Water evaporation behavior was analyzed by measuring change in weight in real time after applying the keratinocyte mimetics prepared in Example 4 and Comparative Examples 4-6. The test was performed in a room maintained at constant temperature and humidity. A desiccator was equipped to control temperature, humidity and air flow. The experiment was carried out under the condition of 25±2° C. and 38±1% humidity.

35 μL of the keratinocyte mimetic was applied onto an area of 5×5 $cm^2$ on artificial leather using a glass plate until it became completely transparent under shear stress.

Starting from immediately after the application, the change in weight for 1 hour was measured with 10-second intervals using an electronic balance (XS204V, capacity: 220 g, readability: 0.1 mg) and the LabX Light Balance 1.5 software. Temperature and humidity were also recorded. At least 3 measurements were made repeatedly for the same sample.

FIG. 6 shows the water evaporation behavior for Example 4 and Comparative Examples 4-6. The evaporation pattern could be divided into an early zone where a linear change is exhibited due to evaporation of free water and a late zone where an exponential change is exhibited due to evaporation of bound water. From the evaporation pattern, the remaining content after 1 hour, i.e. the finally remaining content, and the evaporation rate of bound water, i.e. the slope of the curve in the exponential zone, can be obtained.

These two indices indicate how much water the sample retains continuously. The two indices obtained from FIG. 6 are given in Table 9. As seen from Table 9, the finally remaining content increased in the order of Comparative Example 6<Comparative Example 4<Comparative Example 5<Example 4. The finally remaining content may be directly related to the finally remaining water content in samples having same content of solid.

The slope in the exponential zone, which is the value a in the formula $F=YO+a \times exp^{-bx}$ and is the index related to the evaporation rate of bound water, increased in the order of Example 4<Comparative Example 5<Comparative Example 4<Comparative Example 6. That is to say, the evaporation rate of bound water is the slowest and, accordingly, the finally remaining water content is high in Example 4. The reason why the hydrogel core vesicle of Comparative Example 4 wherein the representative moisturizing ingredient glycerin was contained instead of the natural moisturizing factor showed poor water holding ability may be because glycerin is resoluble in lipid and fails to effectively retain water in the structure. The reason why the hydrogel core vesicle of Comparative Example 5 prepared by the film hydration method showed poor result may be because the natural moisturizing factor cannot be contained effectively as shown in Test Example 3. Lastly, the reason why the natural moisturizing factor of Comparative Example 6 showed the fastest water evaporation is because a barrier to prevent the water evaporation was not formed.

TABLE 9

Indices derived from water evaporation pattern

|  | Final remaining content | Slope of curve in exponential zone |
| --- | --- | --- |
| Example 4 | 30.2 | 34.2 |
| Comparative Example 4 | 15.4 | 36.1 |
| Comparative Example 5 | 17 | 35.9 |
| Comparative Example 6 | 14 | 60.9 |

Test Example 5

Test for Improvement of Skin Moisturization in Human Skin

The effect of improving skin moisturization was measured for the O/W emulsions and soluble gels prepared in Examples 5-6 and Comparative Examples 7-8.

40 male and female adults in their 50s and 60s with dry skin were divided into 4 groups and were asked to apply the cosmetic compositions of Examples 5-6 and Comparative Examples 7-8, respectively, on the face for 4 weeks, twice a day. Before and after the application, on weeks 1, 2 and 4, and 2 weeks after the stopping of the application (on week 6), a skin water content was evaluated using, moisture detector, a corneometer which measures electrical conductivity of the skin under constant temperature and humidity (24° C., RH 40%). The result is given in Table 10.

The values in Table 10 are represented as percentage (%) of increase values measured at regular intervals on a basis of the corneometer value measured before starting the test. Examples 5-6 resulted in remarkably improved skin moisturization as compared to Comparative Examples 7-8.

TABLE 10

Increase in water content after application of cosmetic composition containing keratinocyte mimetic

| | Increase in water content (%) | | | |
| --- | --- | --- | --- | --- |
| | Week 1 | Week 2 | Week 4 | Week 6 |
| Example 5 | 48 | 52 | 50 | 43 |
| Example 6 | 27 | 30 | 32 | 32 |
| Comparative Example 7 | 30 | 32 | 31 | 22 |
| Comparative Example 8 | 19 | 24 | 20 | 15 |

The invention claimed is:

1. A method for preparing hydrogel particles coated with lipid, comprising,
dispersing a lipid in an organic solvent to prepare an organic solvent in which the lipid is dissolved,
dispersing dry hydrogel particles in the organic solvent in which the lipid is dissolved to prepare a dispersion of hydrogel particles in the organic solvent,
adding water to the dispersion of hydrogel particles in the organic solvent to swell the hydrogel particles, and
removing the organic solvent by distilling under reduced pressure to form the hydrogel particles coated with lipid,
wherein the organic solvent comprises a main organic solvent and a $C_1$-$C_6$ alcohol,
wherein the main organic solvent is one or more selected from a group consisting of methylene chloride, chloroform, hexane, heptane, isooctane, cyclohexane, benzene, toluene, xylene and dimethyl ether,
wherein a content of the $C_1$-$C_6$ alcohol is 20-70% of a content of the main organic solvent,
wherein a content of the lipid is 2-10 times a dry weight of the hydrogel.

2. The method for preparing hydrogel particles coated with lipid according to claim 1, wherein the lipid is one or more selected from a group consisting of soybean lecithin, phosphatidylcholine, phosphatidylserine, phosphatidylethanolamine, phosphatidylglycol and hydrogenated phosphatidylcholine.

3. A method for preparing hydrogel particles coated with lipid according to claim 1, wherein the hydrogel particles are prepared by crosslinking a water-soluble polymer, and wherein the crosslinking comprises mixing an oil phase in which a surfactant is dissolved with an aqueous phase in which the water-soluble polymer and a water-soluble crosslinking agent are dissolved.

4. The method for preparing hydrogel particles coated with lipid according to claim 1, wherein said dissolving lipid in the organic solvent of the above (a) further comprises dissolving an oil-soluble active material or drug in the organic solvent.

5. The method for preparing hydrogel particles coated with lipid according to claim 3, wherein the water-soluble polymer of the above (b) is one or more selected from a group consisting of hyaluronic acid and salts thereof, polyvinyl alcohol, polyvinylpyrrolidone, maleic anhydride/vinyl ether copolymer, gelatin, alginate, hydroxyethyl methacrylate, carrageenan, hydroxyethyl cellulose, silicone rubber, agar, hydroxypropyl cellulose, hydroxypropyl methylcellulose, methyl cellulose, carboxyvinyl copolymer, polyethylene oxide, polyethylene glycol, polyacrylamide, poly(hydroxyethyl methacrylate), polydioxolane, polyacrylic acid, polyacryl acetate, polyacrylamide and polyvinyl chloride.

6. The method for preparing hydrogel particles coated with lipid according to claim 3, wherein the crosslinking agent of the above (b) is one or more selected from a group consisting of ethylene glycol, glycerin, polyoxyethylene glycol, calcium chloride, bisacrylamide, diaryl phthalate, diaryl adipate, 1,4-butanediol diglycidyl ether, polyethylene glycol diglycidyl ether, polypropylene glycol diglycidyl ether, triglycerin diglycidyl ether, triarylamine and glyoxal.

7. The method for preparing hydrogel particles coated with lipid according to claim 1, which further comprises, simultaneously with said dispersing dry hydrogel particles or before or after said dry dispersing hydrogel particles, adding a water-soluble active material or drug.

8. The method for preparing hydrogel particles coated with lipid according to claim 4, wherein the active material is selected from a group consisting of L-ascorbic acid and a derivative thereof, epigallocatechin-3-gallate and a derivative thereof, retinol, retinyl acetate, retinyl palmitate, tocopherol, tocopheryl acetate, tocopheryl linoleate, tocopheryl nicotinate, linoleic acid, coenzyme $Q_{10}$, resveratrol, lipoic acid, thymol trimethoxycinnamate, curcumin, tetrahydrocurcumin, oleanolic acid, ursolic acid, betulin, betulinic acid, diosmetin, quercetin, lycopene, kaempferol, luteolin, animal/plant extract, kojic acid and a derivative thereof, ceramide, peptide compound, amino acid, caffeine, water-soluble functional extract and oil-soluble functional extract.

9. The method for preparing hydrogel particles coated with lipid according to claim 7, wherein the water-soluble active material is a natural moisturizing factor.

10. The method for preparing hydrogel particles coated with lipid according to claim 9, wherein the natural moisturizing factor comprises one or more selected from a group consisting of amino acid, sodium pyrrolidone carboxylate, sodium lactate and urea.

11. The method for preparing hydrogel particles coated with lipid according to claim 10, wherein the amino acid comprises one or more selected from a group consisting of serine, glycine, arginine, glutamic acid, tyrosine and alanine.

12. The method for preparing hydrogel particles coated with lipid according to claim 9, wherein a content of the natural moisturizing factor is 5-30 wt % of a content of the hydrogel particles coated with lipid.

13. The method for preparing hydrogel particles coated with lipid according to claim 7, wherein the active material is selected from a group consisting of L-ascorbic acid and a derivative thereof, epigallocatechin-3-gallate and a derivative thereof, retinol, retinyl acetate, retinyl palmitate, tocopherol, tocopheryl acetate, tocopheryl linoleate, tocopheryl nicotinate, linoleic acid, coenzyme $Q_{10}$, resveratrol, lipoic acid, thymol trimethoxycinnamate, curcumin, tetrahydrocurcumin, oleanolic acid, ursolic acid, betulin, betulinic acid, diosmetin, quercetin, lycopene, kaempferol, luteolin, animal/plant extract, kojic acid and a derivative thereof, ceramide, peptide compound, amino acid, caffeine, water-soluble functional extract and oil-soluble functional extract.

* * * * *